US006647764B1

(12) United States Patent
Paul et al.

(10) Patent No.: US 6,647,764 B1
(45) Date of Patent: Nov. 18, 2003

(54) QUARTZ CRYSTAL MICROBALANCE WITH FEEDBACK LOOP FOR AUTOMATIC GAIN CONTROL

(76) Inventors: Frank Paul, GlaxoSmithKline New Frontiers Science Park South Third Ave., Harlow Essex CM19 5A W (GB); Karl Pavey, c/o GlaxoSmithKline New Frontiers Science Park South Third Avenue, Harlow Essex CM19 5A W (GB); Richard C Payne, GlaxoSmithKline The Frythe, Welwyn Hertfordshire AL6 9AR (GB)

( * ) Notice: Subject to any disclaimer, the term of this patent is extended or adjusted under 35 U.S.C. 154(b) by 0 days.

(21) Appl. No.: 09/830,396

(22) PCT Filed: Oct. 21, 1999

(86) PCT No.: PCT/EP99/08148

§ 371 (c)(1),
(2), (4) Date: Jun. 29, 2001

(87) PCT Pub. No.: WO00/25118

PCT Pub. Date: May 4, 2000

(30) Foreign Application Priority Data

Oct. 26, 1998 (GB) .............................................. 9823410

(51) Int. Cl.[7] ........................... G01N 9/00; G01N 11/16
(52) U.S. Cl. .......................... 73/54.41; 73/322; 73/437; 73/32 A; 73/61.79; 73/64.53
(58) Field of Search ............................... 73/32 A, 32 R, 73/54.41, 61.49, 61.79, 64.53, 437

(56) References Cited

U.S. PATENT DOCUMENTS

| 4,783,987 A | 11/1988 | Hager et al. |
| 4,788,466 A | 11/1988 | Paul et al. |
| 5,201,215 A | 4/1993 | Granstaff et al. |
| 5,416,448 A | 5/1995 | Wessendorf |

FOREIGN PATENT DOCUMENTS

| EP | 0 215 669 | 9/1986 |
| WO | WO 09938 | 2/1989 |
| WO | WO 35103 | 11/1996 |

OTHER PUBLICATIONS

Barnes, "Development of quartz crystal oscillators for under–liquid sensing", Sensors and actuators A, 29 (1991) pp. 59–69.

Nakamoto et al., "Development of Circuit for Measuring both Q Variation and Resonant Frequency Shift of Quartz Crystal Microblance", IEEE Trnsactions on Ultrasonics Ferroelectrics and Frequency Control, (1994) Nov., No. 6, pp. 806–811.

Komplin et al., "A high–stability quartz crystal microbalance electrode for simultaneous solution–phase electrochemistry/microgravitometry", Rev. Science Instrument, 64 (6), Jun. 1993, pp. 1530–1535.

Chagnard et al., "An electronic oscillator with automatic gain control: EQCM applications", Elsevier Science S.A., 32 (1996) pp. 129–136.

Rodahl et al., "Quartz crystal microbalance setup for frequency and Q–factor measurements in gaseous and liquid environments", Review of Scientific Instruments, 66 (1995) Jul., No. 7, pp. 3924–3930.

*Primary Examiner*—Daniel S. Larkin

(57) ABSTRACT

An analytical apparatus, such as a quartz crystal microbalance, comprising a piezoelectric sensor and an oscillator circuit, coupled to the sensor, to oscillate at a frequency substantially determined by a resonant frequency of the sensor, and to provide an output signal at the oscillator frequency at an output, the oscillator circuit incorporates means to maintain a substantially constant drive signal to the piezoelectric sensor. Preferably the substantially constant drive signal is maintained by AGC means (33) within a feedback loop of the oscillator. Advantageously the gain control signal is used as an indication of the Q of the piezoelectric sensor. It is desirable that the drive signal to the sensor is substantially sinusoidal since this provides greater accuracy, sensitivity and stability for the apparatus. This can be achieved by ensuring that all the elements in the feedback loop providing signal gain and attenuation are configured to operate in a substantially linear mode.

8 Claims, 6 Drawing Sheets

QUARTZ CRYSTAL MICROBALANCE WITH FEEDBACK LOOP FOR AUTOMATIC GAIN CONTROL

This invention generally relates to a novel device, being an analytical apparatus comprising an oscillating piezoelectric sensor and more particularly to an improved quartz crystal microbalance and the use thereof A quartz crystal microbalance is a device for detecting and measuring very small changes in mass. Its primary components are a quartz crystal and an oscillator circuit coupled to the quartz crystal to produce an output at a resonant frequency of the crystal. The output frequency, which is typically around 10 MHz, is measured to a high degree of accuracy, for example, with a frequency counter. The quartz crystal is, unlike the crystals normally used in electronic circuits, unencapsulated, so that it can interact with its environment. The deposition of small quantities of material onto the crystal changes its resonant frequency and allows the determination of the mass of material deposited. Typically, frequency changes are of the order of a few Hz to a few tens of Hz and changes of the order of nanograms in the mass of material deposited can be detected.

The piezoelectric sensor in research analytical apparatus is typically a thin slice of quartz from an artificially grown crystal, although other piezoelectric materials, such as tourmaline, ethylene diamine tartrate, ADP, KDP, and Rochelle salt can, also be used. Quartz has the advantages of being chemically unreactive and insoluble in water, as well as being relatively temperature insensitive. A typical quartz sensor 10 for a microbalance is shown in FIG. 1. The quartz crystal 16 is typically a circular "AT-cut" with metal electrodes 18 on opposing faces. The electrodes are typically sputtered thin (200 nm) films of gold, silver, or titanium, possibly with a sub-layer for improved adhesion. Lead wires 14 attach to the electrodes and also provides mechanical support for the crystal, as well as some degree of isolation from base 12 of the sensor and lead out wires 15. The crystal is typically around 1 cm in diameter. The change in resonant frequency, $\Delta F$, of an AT-cut quartz crystal of area, A, vibrating in air at fundamental frequency, F, when the mass of the crystal is changed by $\Delta M$, is given approximately by:

$$\Delta F = -2.3 \times 10^6 F^2 \Delta M / A.$$

The quartz crystal microbalance is most frequently used to measure mass, but can also be used to detect changes in the viscosity and/or density of a liquid, since when vibrating in a liquid all these factors effect the vibrational frequency. Thus, the shift in frequency of a quartz crystal on immersion in a liquid, $\Delta F$, is given by:

$$\Delta F = -F_0^{3/2} (\eta_L \rho_L / \pi \mu_Q \rho_Q)^{1/2}$$

Where: $\Delta F$=Change in Frequency
$F_0$=Resonance Frequency
$\eta_L \rho_L$=Liquid absolute density and viscosity
$\mu_Q \rho$=Quartz elastic modulus and density.

A quartz crystal microbalance can be used as a bio-sensor, that is as a device which uses as part of the sensor, or is sensitive to, material of biological origin. Typically, part of one or both electrodes of the sensor are coated with material which is capable of binding with a target bio-molecule or cell. When such a receptor is exposed to the target ("ligand") compound, the ligand is bound to the substrate causing a change in mass $\Delta M$ of the sensor, and/or viscosity/density changes in the local microenvironment and a consequent change in its vibrational frequency.

There is a general need for improvements in the sensitivity and effectiveness of known quartz crystal microbalances. More particularly, the oscillator drive circuits of conventional microbalances lack stability and precision, particularly when the sensor is immersed in a liquid. When a crystal surface is immersed in a liquid the "Q" of the crystal (a measure of the sharpness of the resonance or, equivalently, the energy dissipated per cycle) will drop substantially and the resonant frequency will shift slightly. The Q drop is due to the damping effect caused by the absorption of energy by the liquid; the change in resonant frequency is due to the dynamic mass of the liquid on the crystal face. When a crystal resonates its impedance drops from almost infinity to about 50–200$\Omega$; when immersed the impedance at resonance can be 100 K$\Omega$ or higher. In order that the apparatus can operate with the sensor both in and out of a liquid it is necessary to provide a system with a wide dynamic range to accurately determine the sensor's resonant frequency over this wide range of impedances. Although quartz crystal microbalances have been able to operate in either liquid or air, a difficulty arises when the system is required to operate with the sensor in either medium. Furthermore, when operated in a liquid prior devices often exhibit a lack of stability, sensitivity, and precision, possibly related to the broader resonance and greater energy dissipation of the immersed sensor. Efforts to counteract some of this variability have included using dual matched oscillators, comparing the frequencies of working and reference crystals (Dunham G. C., Benson N. H., Petalenz D. and Janata J., Anal. Chem., 67 (1995) 267–272).

There is also a need for improved screening processes for rapid evaluation of compounds of potentially therapeutic benefit. Pharmaceutical companies typically synthesise thousands of compounds, which are then screened in order to identify those which interact with a target molecule. Typically, one or other of the target and ligand are labelled with a radioactive or fluorescent tag, but such techniques are slow, expensive, and require the handling of dangerous materials, and the labelling may interfere with the receptor-ligand interaction. A further problem is therefore the need for improved screening processes and quartz crystal microbalances promise some advantages in this field. However, in this context it is desirable to have a sensor-oscillator system which is stable even in a flowing liquid and which, in this configuration, is sensitive enough to allow bio-molecular interactions on the surface of the crystal electrode to be monitored in real time.

FIG. 2 illustrates an oscillator circuit 20 for a quartz crystal microbalance, known from Barnes C., Sensors and Actuators A., 29 (1991) 59–69. Quartz crystal 24 is series connected in a feedback path connecting the output of CMOS inverter 22 to its input, thereby forming an oscillator. A one-transistor buffer circuit 26 is coupled to the oscillator and provides an output at 28 to a frequency counter. The oscillator will operate in the range 1.7 to 20 MHz, but in the prior art was used by Barnes at 14 MHz. A quartz crystal microbalance using this circuit exhibits the disadvantages outlined above. The present invention seeks to alleviate the problems of conventional systems by providing an improved oscillator circuit.

Accordingly, we will describe analytical apparatus comprising a piezoelectric sensor and an oscillator circuit, coupled to the sensor, to oscillate at a frequency substantially determined by a resonant frequency of the sensor and to provide an output signal at the oscillator frequency at an output and characterised in that the oscillator circuit incorporates means to maintain a substantially constant drive signal to the piezoelectric sensor. In a preferred embodiment, the analytical apparatus is a quartz crystal microbalance. Preferably, the substantially constant drive signal is maintained by AGC means within a feedback loop of the oscillator, the gain control signal from which can be used as an indication of the Q of the piezoelectric sensor. It is desirable that the drive signal to the sensor is substantially sinusoidal since this provides greater accuracy, sensitivity and stability for the apparatus. This can be achieved by ensuring that all the elements in the feedback loop providing signal gain and attenuation are configured to operate in a substantially linear mode.

We will further describe a method of measuring a characteristic of an oscillating piezoelectric sensor in a fluid medium comprising providing an oscillating drive signal to the sensor and characterised in that the method further comprises controlling the drive signal such that it is maintained at an approximately constant level despite changes in the fluid medium.

We will also describe analytical apparatus comprising a piezoelectric sensor; and an oscillator circuit, coupled to the sensor to oscillate at a frequency substantially determined by a resonant frequency of the sensor, and to provide a first output signal at the oscillator frequency; characterised in that the oscillator circuit comprises means to provide a second output signal correlated to the 'Q' of the sensor.

We will further describe an oscillator circuit comprising a piezoelectric sensor, to oscillate at a frequency substantially determined by a resonant frequency of the sensor and to provide an output signal at the oscillator frequency at an output, the circuit comprising an amplifier with feedback coupling to the output to an input of the amplifier to form a feedback loop through the amplifier; and characterised in that the feedback loop incorporates automatic gain control (AGC) means to maintain a substantially constant drive signal to the piezoelectric sensor.

In order to promote a fuller understanding of these and other aspects of the invention, some embodiments will now be described, by way of example only, with reference to the accompanying drawings in which.

An oscillator is generally constructed by providing an amplifier with feedback.

The conditions for oscillation are that the loop gain should be equal to or greater than unity and that the loop gain phase shift is zero (or an integral multiple of $2\pi$). The latter condition expresses a requirement that a signal propagating through the amplifier and the feedback network must experience a phase delay of one or more whole cycles at the frequency of oscillation. A quartz crystal has a series resonant frequency at which its impedance is zero and a slightly higher parallel resonant frequency at which its impedance is infinite; typically, a circuit incorporating a quartz crystal will oscillate close to the parallel resonant frequency of the crystal.

Figure 1:
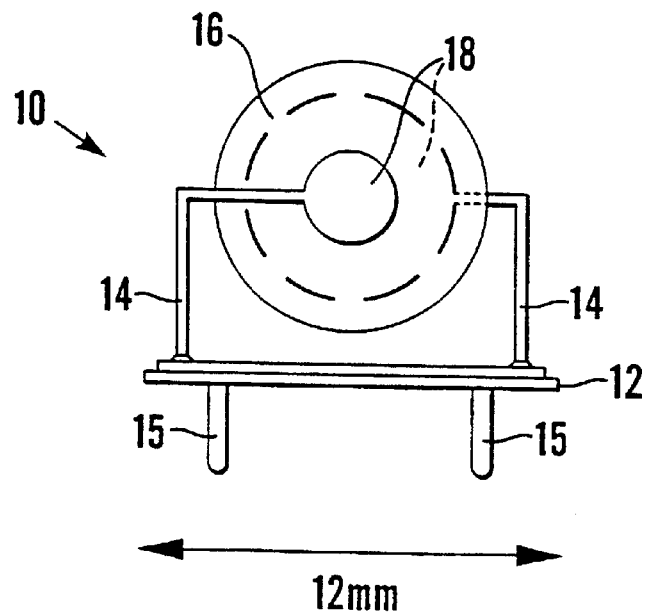
FIG. 1 shows a typical quartz crystal sensor for a microbalance.
Figure 3:
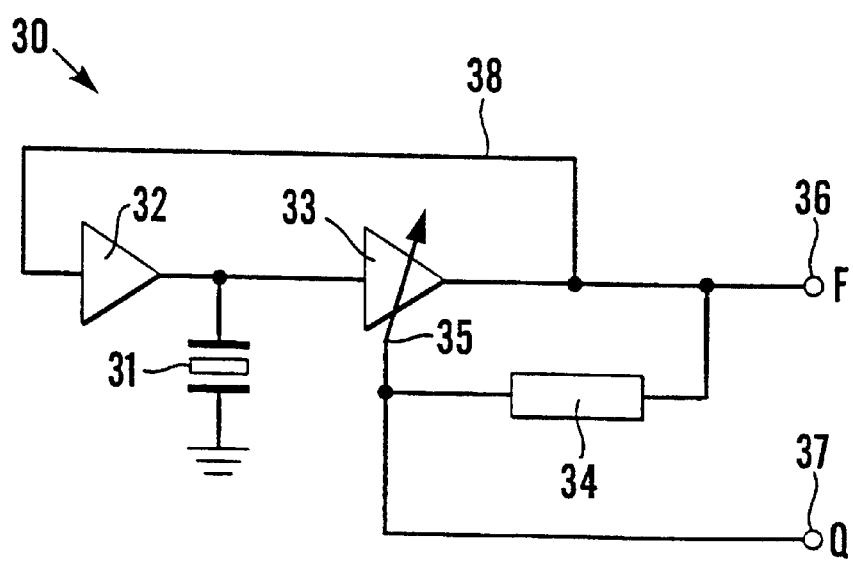
FIG. 3 shows a conceptual block diagram of an improved oscillator circuit.
Figure 2:
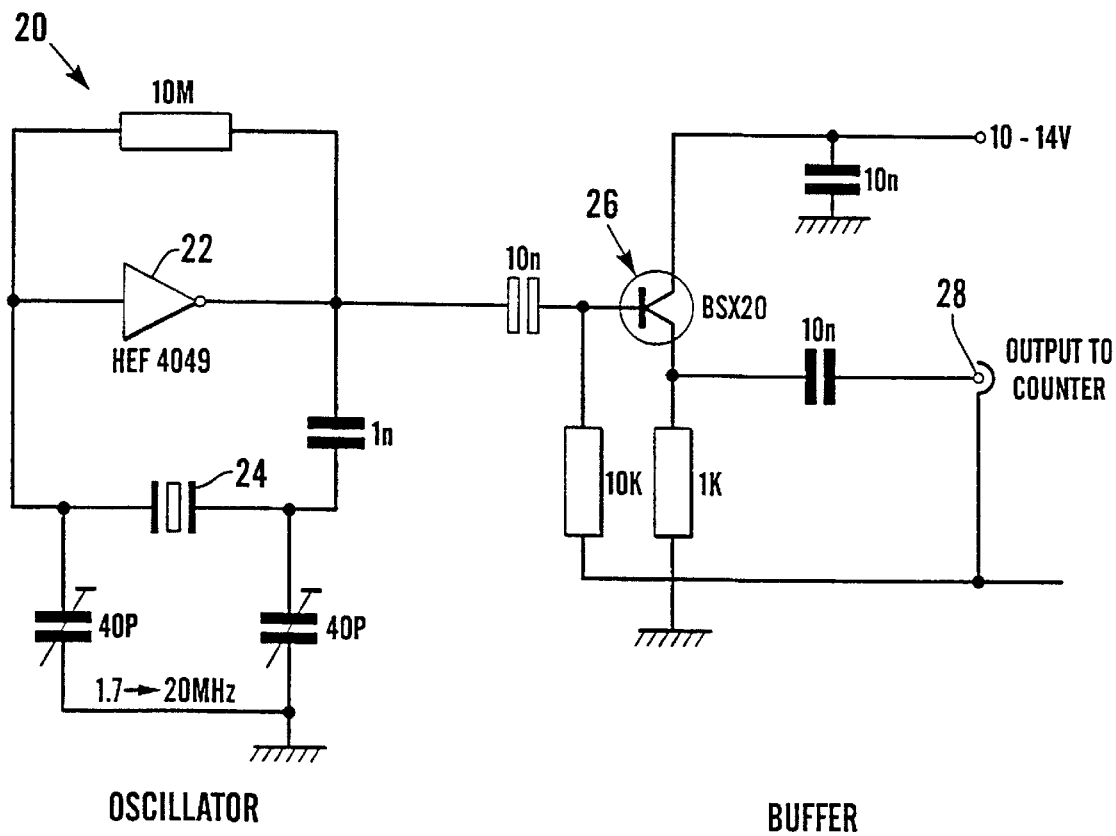
FIG. 2 shows a known quartz crystal oscillator circuit.

In FIG. 3, the conceptual block diagram of an improved oscillator is shown. In this circuit gain is provided by amplifier 32 and automatic gain control (AGC) means 33, 34. The AGC means comprises a variable gain means (amplifier or attenuator) 33 with gain (amplification/attenuation) controllable by a signal on control input 35. It further comprises means 34 to sense the output signal level from the circuit and to control the variable gain means in response to the sensed level. Feedback in the circuit is provided by line 38 which connects the output of the gain/attenuation element 33 to the input of amplifier 32. Quartz crystal 31, which determines the resonant frequency of the oscillator, is connected between the output of amplifier 32 and an earth point, which may be a virtual earth. Alternatively, the circuit can be arranged so that the crystal is series connected. In the parallel-connected configuration shown, in order for crystal 31 to properly determine the resonant frequency of the circuit, the output impedance of the driving circuitry must not be too dissimilar to that of the crystal. Thus, if the amplifier has a low output impedance the crystal can be driven via a resistor, alternatively amplifier 32 may be a transconductance amplifier with a high output impedance. A conventional oscillator will generally include further capacitive and/or inductive tuning elements in series and/or in parallel with the crystal and/or in the feedback path 38. However, in the circuits described herein, it is preferable to reduce such additional elements to a minimum so that the frequency of oscillation is as much as possible determined by the resonant frequency of the crystal alone. It will be seen later that in a preferred embodiment the passive elements of the oscillator drive circuit are, disregarding stray capacitance, almost entirely resistive.

Loop gain is provided by the combination of amplifier 32 and AGC means 33; one or other of these elements may provide some or all of the gain. In operation, the output of amplifier 32 drives crystal 31 at the resonant frequency and a signal at this frequency appears at output 36. The signal level at output 36 is monitored by level sensing means 34 which is coupled to the gain control input 35 of AGC means 33 to control the loop gain. Since the output of AGC means 33 is fed back to the input of amplifier 32, a substantially constant drive at the frequency of oscillation is maintained to crystal 31. A substantially constant signal level is also maintained at output 36. When used with a quartz crystal microbalance or similar apparatus, maintaining the level of drive signal to quartz crystal, which in the general case is any form of piezoelectric sensor, provides a number of advantages. The improved drive circuit is capable of maintaining sensor oscillation whilst the sensor is in a range of different or varying environments—for example, air liquid, and flowing liquid. In a liquid, as described above the additional damping decreases the Q of the sensor and in the system of FIG. 3 the oscillator automatically compensates for this Q reduction.

It has also been found that it is important to provide a substantially sinusoidal drive signal to the crystal. When the crystal is damped, for example by a liquid, if a significantly non-sinusoidal or square wave is driving it, there is a tendency for the crystal to hop to an overtone frequency. This tendency is reduced with a sinusoidal drive. The oscillator drive and feedback circuitry (in FIG. 3, amplifier 32 and AGC means 33) is therefore preferably linear. In a preferred embodiment described below, all the amplifiers in the relevant part of the oscillator, that is those involved in providing a high frequency drive to the crystal are linear, and preferably have low distortion.

The features described above assist the oscillator in locking more precisely onto the resonant frequency of the sensor, especially in "difficult" or liquid environments, thus providing a quartz crystal microbalance with improved sensitivity and robustness of use. Furthermore, this oscillator design can more easily follow frequency changes such as occur when, for example, detecting the binding of a ligand to the crystal and a substrate thereon.

It has been found that the level of the AGC control signal can be correlated with the 'Q' of the sensor and hence this control signal is also provided at a separate output 37. In the detailed circuit described with reference to FIG. 6, a DC level proportional to the sensor Q value is provided at this output. It has also been found that the sensor Q value can empirically be related to the viscosity of a fluid in which the sensor is immersed and the Q output can therefore be used to provide a direct indication of this viscosity. Accordingly in a preferred embodiment of the invention, changes in frequency and Q value are monitored to obtain useful information concerning material subjected to analysis using the sensor.

In FIG. 3, the crystal 31 has been shown connected in parallel with the amplifier output, but the skilled person will understand that the crystal could also be connected at other positions in the circuit and could, for example, be series connected.

Figure 4A:
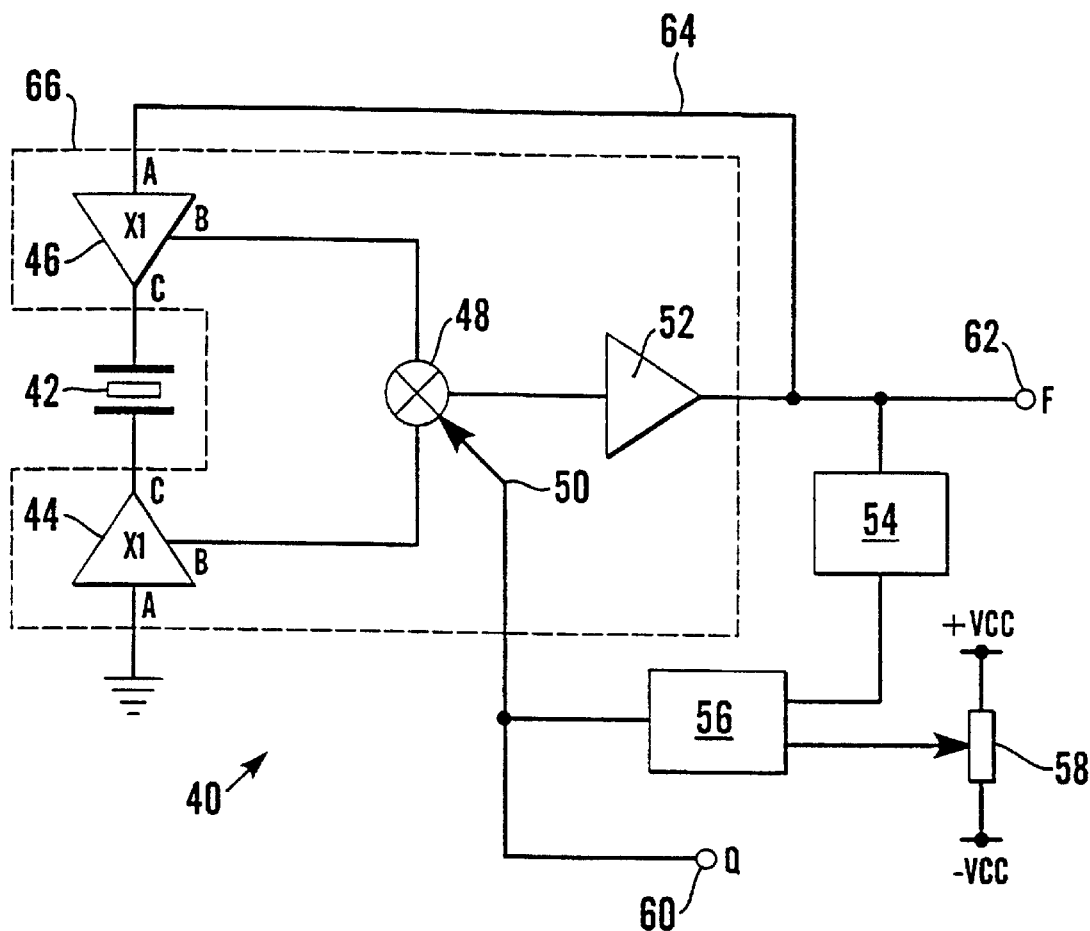
FIG. 4a shows a block diagram of a preferred embodiment of an oscillator in accordance with the present invention.

Referring now to FIG. 4a, a block diagram of a preferred embodiment of an oscillator 40 is shown, based on the conceptual arrangement of FIG. 3. Like the conceptual system, the oscillator of FIG. 4a includes a piezoelectric sensor 42 driven by an amplifier 46, although in a preferred system this amplifier has unity gain and serves as a buffer. In the embodiment shown, amplifier/buffer 46 has two outputs, one driving the sensor 42, the second forming one input to a two-quadrant multiplier 48 which is voltage controlled by input 50 and operates as a voltage controlled attenuator. In a specific embodiment, amplifier 46 provides a current drive to a quartz crystal 42 and this current is mirrored to provide an input to the two-quadrant multiplier. In the arrangement of FIG. 4a a second terminal of the sensor 42 is also driven by amplifier 44, which similarly to amplifier 46, provides an output to a second input of the two-quadrant multiplier 48. Again, amplifier 44 is preferably a unity gain buffer. The output of multiplier 48 is further amplified by amplifier 52, preferably an operational amplifier and, as in the conceptual arrangement of FIG. 3, a positive feedback path 64 is provided to the input of amplifier/buffer 46. The output of amplifier 52 is made available at an output terminal 62; this provides a signal at the frequency of oscillation for input to a frequency counter.

The output of amplifier 52 is also coupled to rectifier means 54 which detects the signal level and integrator/comparator means 56 which, inter alia, smooths variations of signal level and integrates over a number of cycles. The signal level at the output 62 is compared with a signal level amplitude set on adjustment means 58, which is preferably a potentiometer. The output of integrator 56 is coupled to the "gain" control input 50 (in a preferred embodiment, an attenuation control input) to maintain an approximately constant level of output signal output 62 and to maintain the drive signal to piezoelectric sensor 42. This control signal is, in a preferred embodiment, a DC level, made available at output 60 and proportional to the Q of the sensor.

The elements shown enclosed by dashed line 66 are available in a single integrated circuit package, which improves the matching between circuit elements and provides additional advantages of reduced circuit size and power consumption. An integrated circuit, such as the Comlinear CLC 520 or CLC 522 available from National Semiconductor Corporation, can be used. When the oscillator output is rectified and compared with the amplitude reference voltage and the result applied to what can be termed "cell gain control input", a substantially pure sinusoidal oscillation around the crystal resonance is generated with a tight control over loop gain. When the sensor Q falls, the output reduces, thus increasing the input to the gain cell and increasing the loop gain to compensate, so keeping the resonance constant. In the circuit of FIG. 4a, the two-quadrant multiplier 48 functions as a "gain cell". The feedback path 64 applies positive feedback and the circuit therefore resonates at a resonant frequency of the piezoelectric sensor.

Figure 4B:
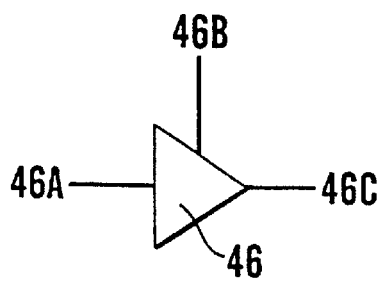
FIG. 4b shows an input amplifier for an oscillator.

FIG. 4b illustrates the connections to input amplifier 46. This amplifier is unusual in that it has a single input 46A, but two outputs, 46B and 46C. The functioning of this amplifier was outlined above, but, it is helpful to consider another equivalent way of looking at its function. The output 46B reflects the reactance of a load imposed on the second (intermediate) output 46C, so that the impedance placed on output 46C controls the gain between input 46A and output 46B. In the preferred embodiment, there is unity gain between 46A and 46C, but variable gain between 46A and 46B. Amplifier/buffer 44 is similar.

Figure 5:
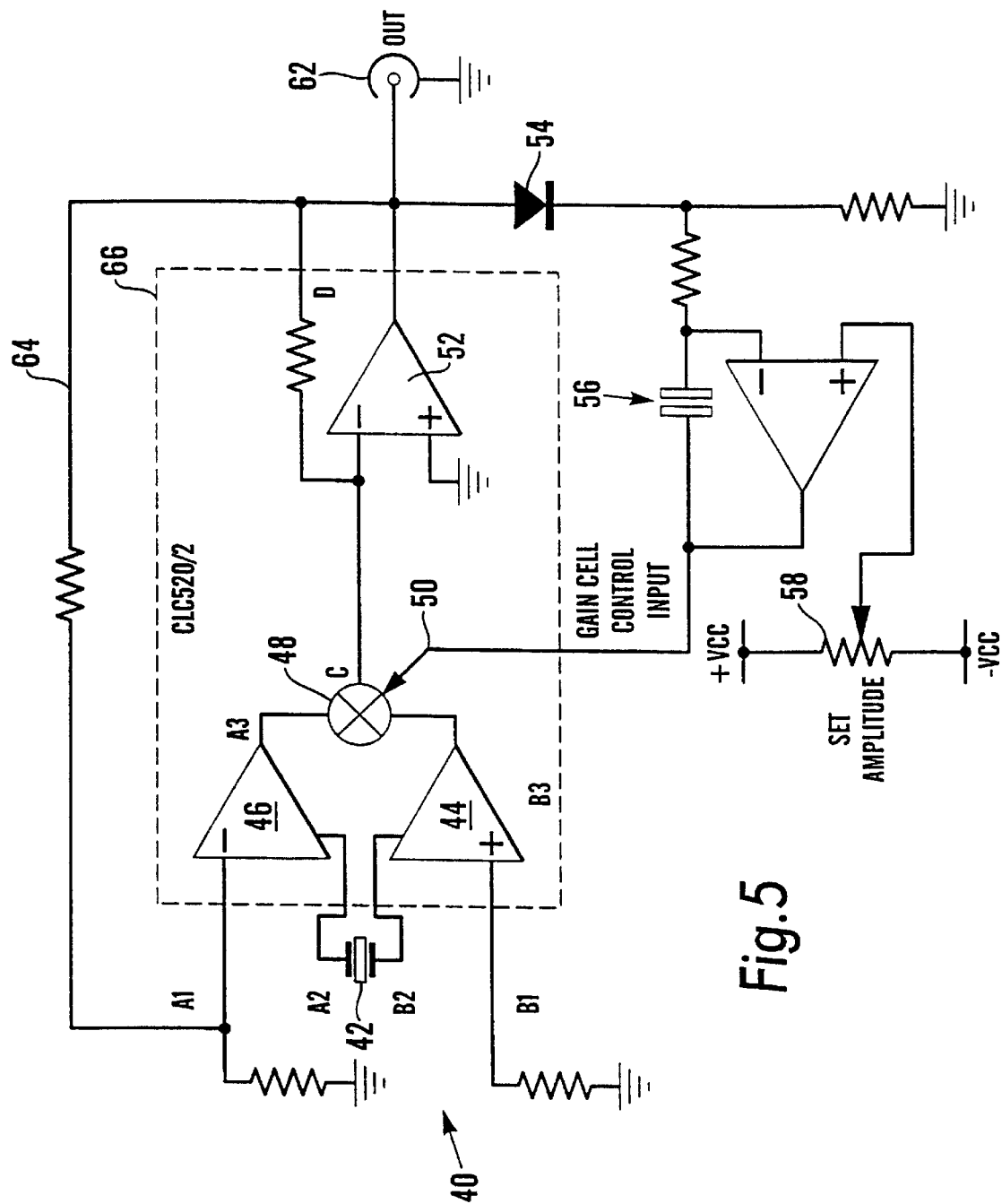
FIG. 5 shows a detailed circuit diagram of a first embodiment of an oscillator in accordance with the present invention.

FIG. 5 shows a detailed circuit diagram of a basic oscillator circuit constructed in accordance with the block diagram of FIG. 4a. In FIGS. 4 to 7, like elements are indicated by the same reference numerals. Thus, the main elements of FIG. 4a can be identified in FIG. 5, that is crystal 42, amplifiers 44 and 46, multiplier 48 with attenuation/gain control input 50, amplifier 52, positive feedback path 64, rectifying means 54, integrator/comparator 56, and output level adjust means 58.

The two input buffers 44 and 46 convert the input voltage to a current that is a function of the differential input voltage and the value of the gain-setting impedance of crystal 42. This current is then mirrored to a gain stage (not shown) and attenuated by to voltage controlled two-quadrant multiplier 48, after which it is converted to a voltage by output amplifier 52 with gain set by feedback resistor R4. Thus, the input, output, and gain control signals are all voltages.

An output at the oscillator frequency is provided at 62 and the components within the dashed line 66 can be obtained within a single integrated circuit. In the detailed circuit shown, it can be seen that amplifier 46 has an inverting input whilst amplifier 44 has a non-inverting input, and that amplifier 52 is an operational amplifier. Rectifier means 54 can at its simplest, be a single diode and the integrator/comparator 56 can again be constructed from a single operational amplifier. The skilled person will be aware that many variations on these basic circuit elements are possible. For example, other rectifying elements or more sophisticated full wave rectifiers could be used for the rectifier means. Many conventional variations are possible on integrator means 56 and tuned elements could be incorporated in series or in parallel with the crystal and/or in feedback loop 64, or alternatively, additional reactive (inductive or capacitive or resistive) components could be included in these positions.

Figure 6:
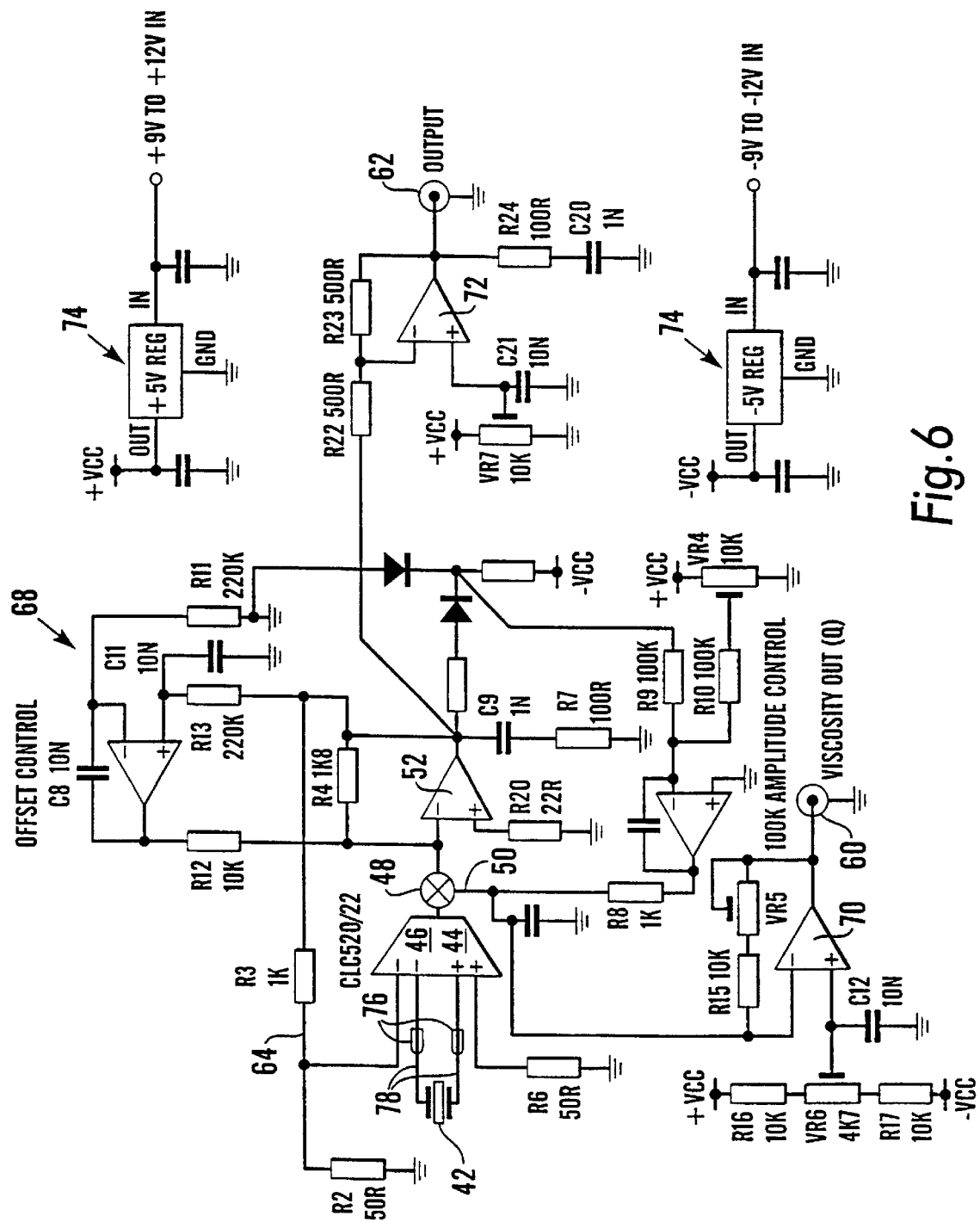
FIG. 6 shows a detailed circuit diagram of a second embodiment in accordance with the present invention.

FIG. 6 shows a detailed circuit of an embodiment incorporating various additions desirable in a practical implementation. It can be seen that this circuit closely corresponds to that of FIG. 5, with the addition of amplifiers/buffers 70 and 72 for the Q output 60 and the frequency output 62 respectively. Additional (low pass) filtering 68 has also been incorporated in a second feedback path from the output of amplifier 52 back to its inverting ("−") input. Positive and negative 5 volt power supplies 74 are also shown. In FIG. 6, connections to the sensor 42 are made via terminal 76 and connecting wires 78. Wires 78 may be, for example, a screened cable or a balanced twisted-pair type connection. Connectors 76, which may be a single connector, are chosen in accordance with conventional practice, to be suitable for relatively low-level high frequency (1–100 MHz) signals.

Figure 7:
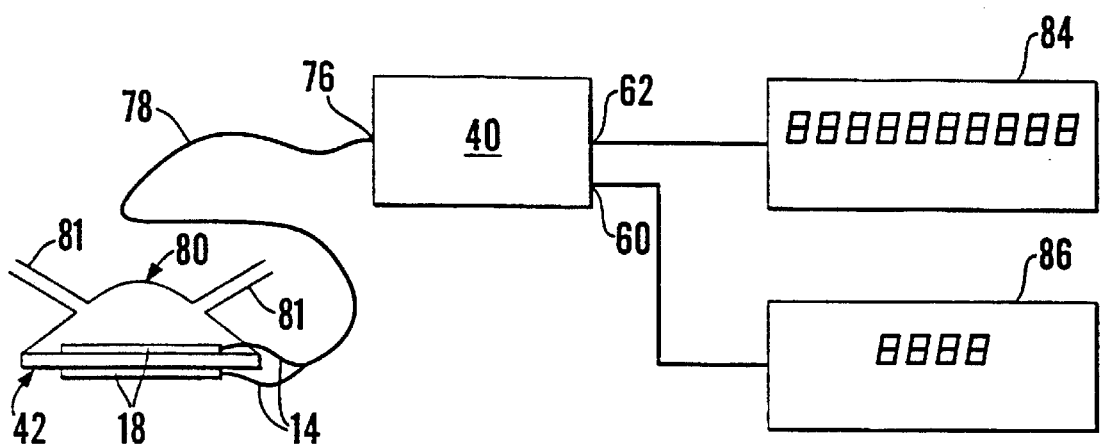
FIG. 7 shows a quartz crystal microbalance incorporating an improved oscillator circuit.

FIG. 7 shows one example of a complete quartz crystal microbalance including oscillator 40 coupled via connection 76 and wires 78 to crystal sensor 42 in a flow cell 80, with fluid inlet and outlet connections 81. The flow cell is preferably arranged so that fluid flowing through the cell contacts only a single face of the sensor, to improve the system performance when used with ionic, and hence conducting fluids, although the sensor may also be configured to operate in a fluid bath.

Figure 8:
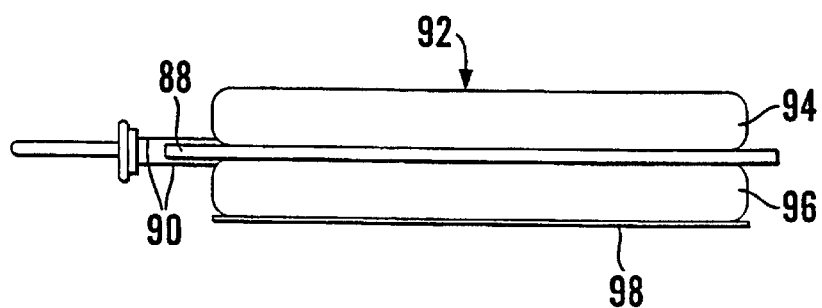
FIG. 8 shows a quartz crystal sensor cell.

The frequency output 62 is coupled to a digital frequency counter 84 with a resolution of the order of 1 Hz; the Q output 60 is coupled to digital voltmeter 86. FIG. 8 shows an alternative arrangement of a sensor with quartz crystal 88 with lead wires 90 sandwiched between O-rings 94 and 96 and resting on a cover slip 98. This arrangement provides a well 92 which can be partially filled with liquid; a simpler configuration can dispense with cover slip 98 and lower O-ring 96. Generally speaking, gold sensor electrodes are preferred because of their reduced tendency to oxidise.

A quartz crystal microbalance such as that shown in FIG. 7, can be used for a variety of purposes. The apparatus is sensitive, among other things, to the density and viscosity of a liquid in which the sensor is immersed and can detect small mass changes even where a large tare is necessary to take account of initially deposited material. One actually constructed circuit was found to be stable to ¼ Hz/day, obviating a need for a reference crystal. The apparatus can also detect the binding of ligands of much smaller molecular weight than is possible with conventional quartz crystal microbalances, allowing direct screening of potential drug candidates. For example, the circuits described herein allow the detection of binding of ligands of molecular weight less than 600, for example ligands of molecular weight circa 180 or less, such as glucose.

The apparatus can be used to provide improved immunoassay apparatus. A typical immunoassay involves detecting the binding of an antigen to an antibody, or of a receptor to a ligand. One immunoassay process, known as the Bayston test (Bayston R., J. Clin. Path., 25 (1972) 718–720), relies on the antibody-antigen binding process in solution to form aggregates or clumps producing a visible precipitate. This process can be monitored using a quartz crystal microbalance, which is thought to respond to changes in the viscosity and density of the medium supporting the antibody and antigen. These changes cause a drop in the resonant frequency of the sensor, the largest drop occurring at the point of full agglutination and hence a quartz crystal microbalance simplifies detection of the titre of agglutination.

The improved quartz crystal microbalance can be used to monitor the characteristics of bacteria in solution. For example, one face of the piezoelectric sensor is coated with fibronectin to which bacteria such as Staphylococcus Epidermidis will bind. The microbalance also has the required sensitivity and robustness for a real time monitoring system to allow continuous assay of a sample, for example, to determine the number of cells in a solution. In such a configuration, the shift in resonant frequency of the sensor has been found to be related to the bacterial concentration, with a roughly linear relationship between the frequency shift and a logarithm of the bacterial concentration. In both this and the previous example, local changes in solution viscosity and density in the region of the electrode surface are believed to influence the resonant frequency of the sensor. It is believed that this effect is present even when there is no actual binding of a species directly to the crystal surface, but merely a local modification to the liquid around the vibrating sensor.

The apparatus can also be used to investigate binding and similar processes as they occur in complete or substantially complete cells. The cells can be grown onto the sensor following which the small additional mass changes due to binding and transport mechanisms at a cell surface can be monitored if desired, in vivo. This is possible because of the ability of the oscillator circuit to follow large changes in the resonant frequency of the crystal whilst maintaining oscillation and maintaining the sensitivity of the system to very small mass changes. Similarly, relatively thick multi-layer structures—for example 20 layers of protein—can be built up on the sensor before binding events are monitored.

Although some examples of possible applications of the invention have- been given many other alternatives will occur to those skilled in the relevant arts and it should be understood that the present invention is not limited to the illustrated embodiments. Likewise, many other effective alternative configurations of the described oscillator circuit can be envisaged and again it should be understood that the design of the circuit is not limited to those particular versions described and illustrated.

What is claimed is:

1. Analytical apparatus comprising a piezoelectric sensor; and an oscillator circuit, coupled to the sensor to oscillate at a frequency substantially determined by a resonant frequency of the sensor, and to provide an output signal at the oscillator frequency at an output, wherein the oscillator circuit incorporates means to maintain a substantially constant drive signal to the piezoelectric sensor, wherein the oscillator circuit includes an amplifier with feedback coupling the output to an input of the amplifier to form a feedback loop through the amplifier, wherein the feedback loop incorporates automatic gain control (AGC) means, and wherein the AGC means comprises rectification means, integrator means, and variable gain means responsive to the integrator means.

2. Apparatus as claimed in claim 1 further comprising a second output to provide an output signal corresponding to a gain control signal of the AGC means.

3. Apparatus as claimed in claim 1 wherein the drive signal is substantially sinusoidal.

4. Apparatus as claimed in claim 3 wherein the oscillator circuit includes an amplifier with feedback coupling the output to an input of the amplifier to form a feedback loop, and all elements in the feedback loop providing signal gain and attenuation are configured to operate in a substantially linear mode.

5. Apparatus as claimed in claim 1 wherein the piezoelectric sensor comprises a quartz crystal.

6. Apparatus as claimed in claim 1 wherein a structure or compound which interacts with a material of chemical or biological origin is attached to a surface of the crystal or to an electrode on the crystal.

7. Analytical apparatus comprising a piezoelectric sensor; and an oscillator circuit, coupled to the sensor to oscillate at a frequency substantially determined by a resonant frequency of the sensor, and to provide an output signal at the oscillator frequency at an output, wherein the oscillator circuit incorporates means to maintain a substantially constant drive signal to the piezoelectric sensor, and wherein the piezoelectric sensor has two terminals, both of which are actively driven.

8. Analytical apparatus comprising a piezoelectric sensor; and an oscillator circuit, coupled to the sensor to oscillate at a frequency substantially determined by a resonant frequency of the sensor, and to provide an output signal at the oscillator frequency at an output, wherein the oscillator circuit incorporates means to maintain a substantially constant drive signal to the piezoelectric sensor, wherein the oscillator circuit includes an amplifier with feedback coupling the output to an input of the amplifier to form a feedback loop through the amplifier, wherein the feedback loop incorporates automatic gain control (AGC) means, and wherein the oscillator circuit incorporates a second feedback loop comprising filter means.

* * * * *

UNITED STATES PATENT AND TRADEMARK OFFICE
CERTIFICATE OF CORRECTION

PATENT NO. : 6,647,764 B1
DATED : November 18, 2003
INVENTOR(S) : Frank Paul et al.

It is certified that error appears in the above-identified patent and that said Letters Patent is hereby corrected as shown below:

Column 1,
Line 52, the equation should read -- $\Delta F = -F_0^{\frac{3}{2}}(\frac{\eta_L \rho_L}{\pi \mu_Q \rho_Q})^{\frac{1}{2}}$ --

Line 57, "$\mu_Q \rho$" should read -- $\mu_Q \rho_Q$ --

Column 8,
Line 26, "have- been" should read -- have been --.`

Signed and Sealed this

Twenty-fourth Day of May, 2005

JON W. DUDAS
*Director of the United States Patent and Trademark Office*